United States Patent [19]

Mumford et al.

[11] Patent Number: 4,569,350
[45] Date of Patent: Feb. 11, 1986

[54] SYSTEM FOR DETECTING PACER MEDIATED TACHYCARDIA

[75] Inventors: Van E. Mumford; Louis Sasmor, both of Miami, Fla.

[73] Assignee: Cordis Corporation, Miami, Fla.

[21] Appl. No.: 678,332

[22] Filed: Dec. 5, 1984

[51] Int. Cl.[4] .............................................. A61N 1/36
[52] U.S. Cl. ................................. 128/697; 128/419 PT
[58] Field of Search .................. 128/419 PG, 419 PT, 128/697

[56] References Cited

U.S. PATENT DOCUMENTS

| 4,412,541 | 11/1983 | Schaldach et al. | 128/419 PG |
| 4,429,697 | 2/1984 | Nappliolz et al. | 128/419 PG |
| 4,432,362 | 2/1984 | Leckrone et al. | 128/419 PG |
| 4,452,248 | 6/1984 | Keller, Jr. | 128/419 PG |
| 4,505,276 | 3/1985 | Markowitz et al. | 128/419 PT |

Primary Examiner—William E. Kamm
Attorney, Agent, or Firm—George H. Gerstman

[57] ABSTRACT

A system is provided for detecting pacer mediated tachycardia. Atrial electrical signals (P waves) are sensed and ventricular electrical signals (R waves) are sensed. When a P wave is sensed, after a predetermined AV delay, a stimulating pulse is provided to the ventricle if no R wave is sensed during the AV delay. A threshold rate is selected for the sensed PP interval. If the ventrical has been stimulated and the threshold rate is exceeded for a selected number of PP intervals, the AV delay is increased by a predetermined time (delta). A determination is made whether the next sensed PP interval has increased by delta. If the next sensed PP interval has increased by delta, then pacer mediated tachycardia has occurred.

In another embodiment, if the threshold rate is exceeded for a selected number of PP intervals, and the ventricle has been stimulated, then the sensed PP interval is measured and the AV delay is increased to a desired minimum PP interval minus the actual measured PP interval. If the rate continues to be greater than the threshold on the next heartbeat, then pacer mediated tachycardia is not present, and the initial AV delay is reestablished.

7 Claims, 7 Drawing Figures

SYSTEM FOR DETECTING PACER MEDIATED TACHYCARDIA

BACKGROUND OF THE INVENTION

The present invention concerns a novel system for detecting pacer mediated tachycardia.

In cardiac pacers in which electrical signals from the atrium are sensed and the ventricle is stimulated after a selected AV delay, the possibility of a pacer mediated tachycardia exists where there is retrograde conduction of the ventricular stimuli. To understand this phenomenon more clearly, reference is made to FIG. 1. For purposes of this discussion, it will be assumed that the pacer is operating in a demand mode, such as a DVI mode or a DDD mode. For simplicity, only the P waves and R waves of the heart's electrical waveform are illustrated. The upwardly-pointing arrows signify sensing and the downwardly-pointing arrows signify a stimulating pulse.

In FIG. 1 there is a normal heartbeat. The P wave is sensed at time 10 in the atrial channel and after an AV delay 14, the R wave is sensed at time 16 in the ventricular channel 18. Under these conditions, no pacing pulses are generated. In FIG. 2, however, there is AV block. Thus, the P wave is sensed in the atrial channel, but no R wave is sensed in the ventricular channel during a selected AV delay 14. Therefore, a stimulus is provided to the ventricle at time 16 which is the end of the selected AV delay.

FIG. 3 also illustrates an AV block situation. However, in FIG. 3 there is retrograde conduction 19 whereby the ventricular stimulus 20 conducts back to the atrium and, at time 22, the electrode in the atrium senses the retrograde P wave that has been caused by the pacer stimulus. Since no R wave is detected during the next AV delay 14a, at the end of the AV delay 14a another stimulus 24 is provided to the ventricle. Again, this other stimulus 24, if there is retrograde conduction, conducts back to the atrium causing the atrial electrode to sense another retrograde P wave at time 26. The cycle will repeat, resulting in tachycardia that is pacer mediated.

Referring now to FIG. 4, a heartbeat rate that is equal to the heartbeat rate of FIG. 3 is illustrated, although the FIG. 4 heartbeat is sinus tachycardia, not pacer mediated tachycardia.

It is, therefore, an object of the present invention to determine whether a detected tachycardia is pacer mediated.

Another object of one embodiment of the present invention is to modify the pacer operation in the event that the tachycardia is pacer mediated.

Other objects and advantages of the present invention will become apparent as the description proceeds.

SUMMARY OF THE INVENTION

In accordance with the present invention, a system is provided for detecting pacer mediated tachycardia. The system comprises the steps of sensing electrical signals from the atrium and sensing electrical signals from the ventricle. A stimulating pulse is provided to the ventricle, at a first predetermined time after an electrical signal from the atrium is sensed, if no electrical signal from the ventricle is sensed within the first predetermined time. A threshold rate for the interval between sensed electrical signals from the atrium is selected. A detection is made whether the threshold rate is exceeded for a selected number of electrical signals from the atrium. If the threshold rate is exceeded for the selected number of electrical signals from the atrium, then the first predetermined time is increased by a second predetermined time. A determination is then made whether the interval between sensed electrical signals from the atrium has increased by the second predetermined time. If the interval between sensed electrical signals from the atrium has increased by the second predetermined time, this indicates that pacer mediated tachycardia has occurred.

In the illustrative embodiment, the system also includes the step of determining if a stimulating pulse has been provided to the ventricle prior to the step of increasing the first predetermined time by the second predetermined time.

In another embodiment of the invention, if the threshold rate is exceeded for the selected number of electrical signals from the atrium and it is determined that a stimulating pulse has been provided to the ventricle, then the first predetermined time is increased by a minimum desired time interval between sensed electrical signals from the atrium minus the actual sensed time interval between electrical signals from the atrium. It is then detected whether the threshold rate is exceeded for the next heartbeat. If the threshold rate is exceeded for the next heartbeat, this indicates a pacer mediated tachycardia is not present, and then the first predetermined time interval is reestablished. On the other hand, if the rate on the next heartbeat is less than threshold, this indicates pacer mediated tachycardia but the pacer has been modified to prevent the rate from exceeding a desired rate.

A more detailed explanation of the invention is provided in the following description and claims, and is illustrated in the accompanying drawings.

DETAILED DESCRIPTION OF THE ILLUSTRATIVE EMBODIMENT

The system of the present invention will be discussed using the operation of a DDD mode cardiac pacer. An example of a prior art DDD mode cardiac pacer capable of being programmed to operate in the manner described in the present specification is disclosed in Vollmann U.S. Pat. No. 4,467,810. In the DDD mode, a sensing and pacing electrode is connected to the atrium and a pacing and sensing electrode is connected to the ventricle. When a P wave is sensed, no atrial stimulus is issued and an atrial refractory period is provided during which sensed P waves are ignored. When the P wave is sensed, however, after a selected AV delay the ventricle is stimulated. However, if an R wave is sensed during the AV delay, the stimulating pulse to the ventricle is inhibited. When an R wave is sensed or when a stimulating pulse is issued to the ventricle, the timing cycle is reset.

Figure 1:
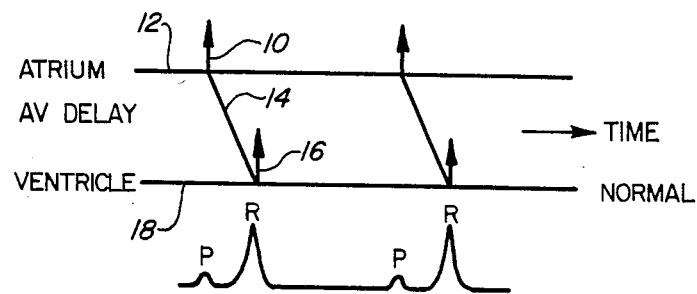
FIG. 1 is a schematic diagram of a pacer operation during a normal heartbeat.
Figure 2:
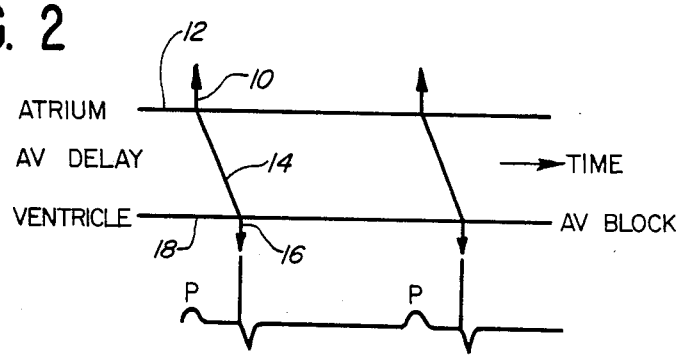
FIG. 2 is a schematic diagram of a pacer during AV block.
Figure 3:
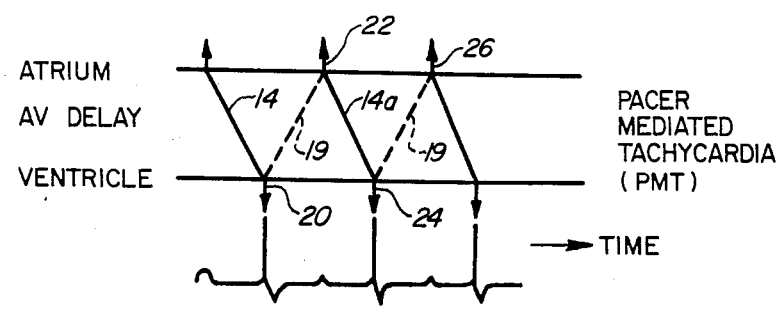
FIG. 3 is a schematic diagram of a pacer during AV block and generating a pacer mediated tachycardia.
Figure 4:
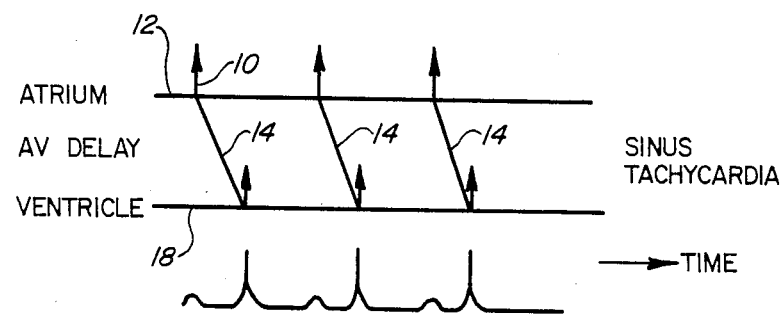
FIG. 4 is a schematic diagram of the operation of a pacer during a sinus tachycardia condition.
Figure 5:
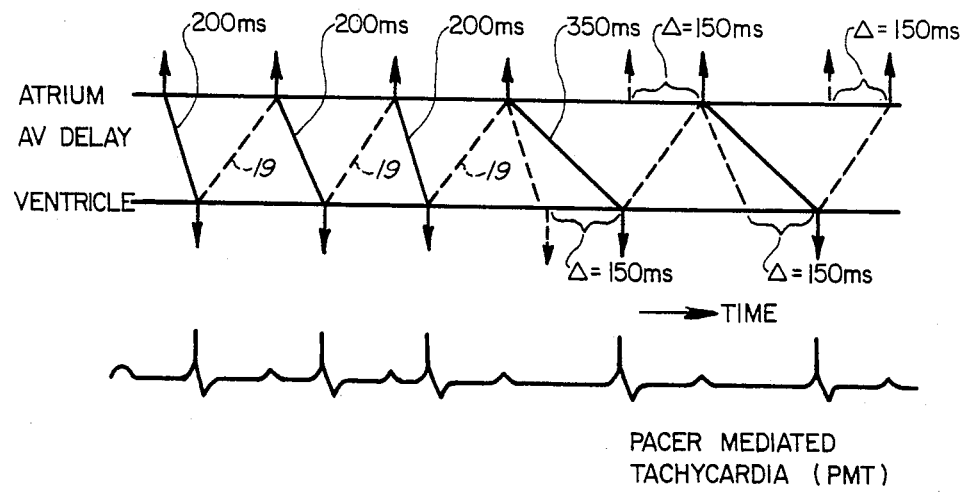
FIG. 5 is a schematic diagram of a pacer operation including the system for detecting pacer mediated tachycardia in accordance with the principles of the present invention.
Figure 6:
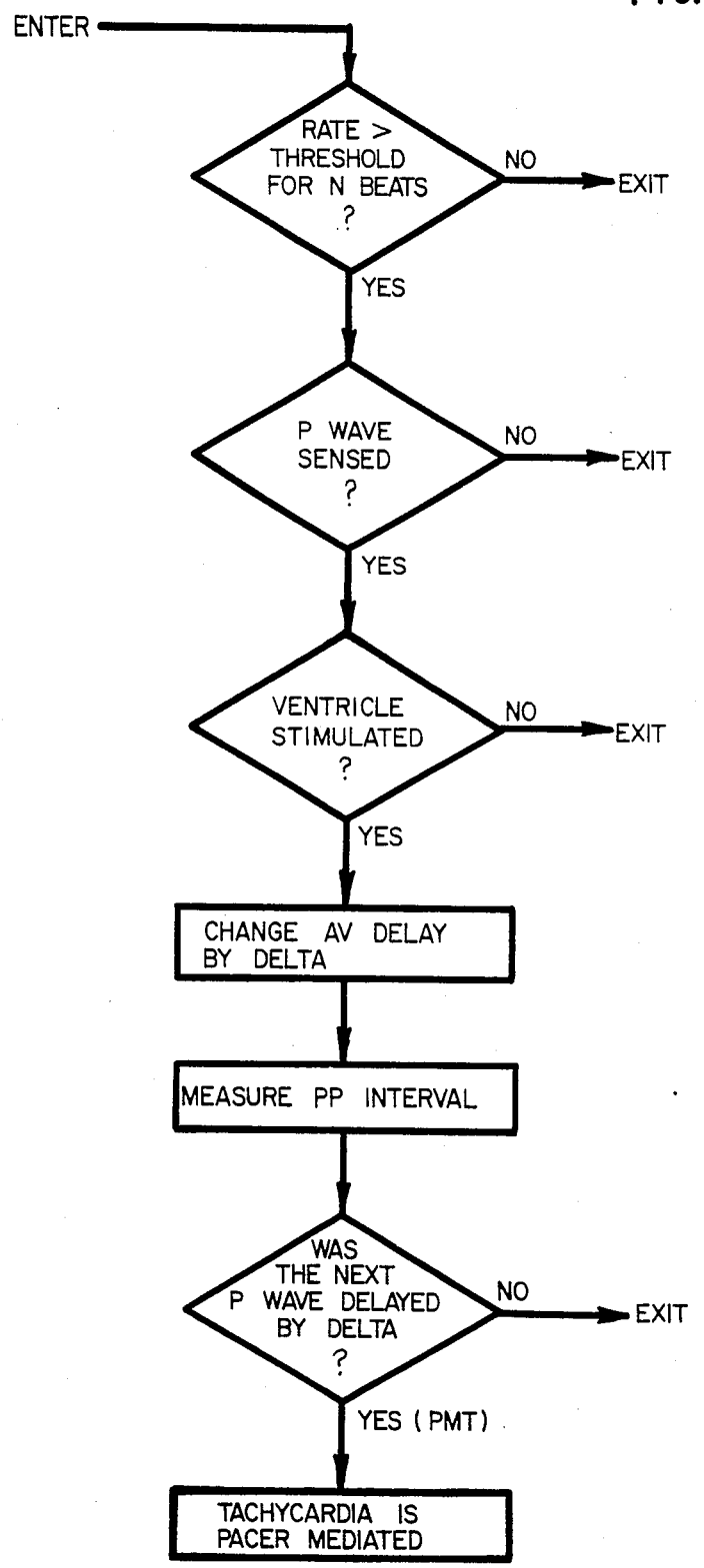
FIG. 6 is a flow diagram of a system for detecting pacer mediated tachycardia.

In order to determine whether there is pacer mediated tachycardia, referring to FIGS. 5 and 6, a threshold rate for sensed P waves is selected, for example, 130 beats per minute. A determination is then made whether this threshold rate is exceeded for a selected number of beats, for example, four beats. If the threshold rate is exceeded for four beats, after the next P wave is sensed a determination is made whether the ventricle has been stimulated at the end of the AV delay. If the ventricle has been stimulated, the AV delay is then changed by a selected amount (delta), for example, 150 milliseconds. Thereafter, the interval between P waves is measured. If the interval between P waves is now greater by 150 milliseconds than the previous interval between P waves, as shown in FIG. 5, this will indicate that the tachycardia is pacer mediated. On the other hand, if the interval between P waves remains substantially the same as the interval between P waves prior to the increase of the AV delay, this indicates that there is no pacer mediated tachycardia.

If there is pacer mediated tachycardia, one method of modifying the problem is to provide an extended atrial refractory period on the next cycle for a substantial time, for example, 500 milliseconds, beyond the ventricular stimulus, to mask the detection of the retrograde P wave.

Another method of correcting for pacer mediated tachycardia is to stimulate the atrium shortly after the detection of the retrograde P wave, to cause the depolarization of the reentry path and to make retrograde conduction impossible following the next ventricular stimulus.

Figure 7:
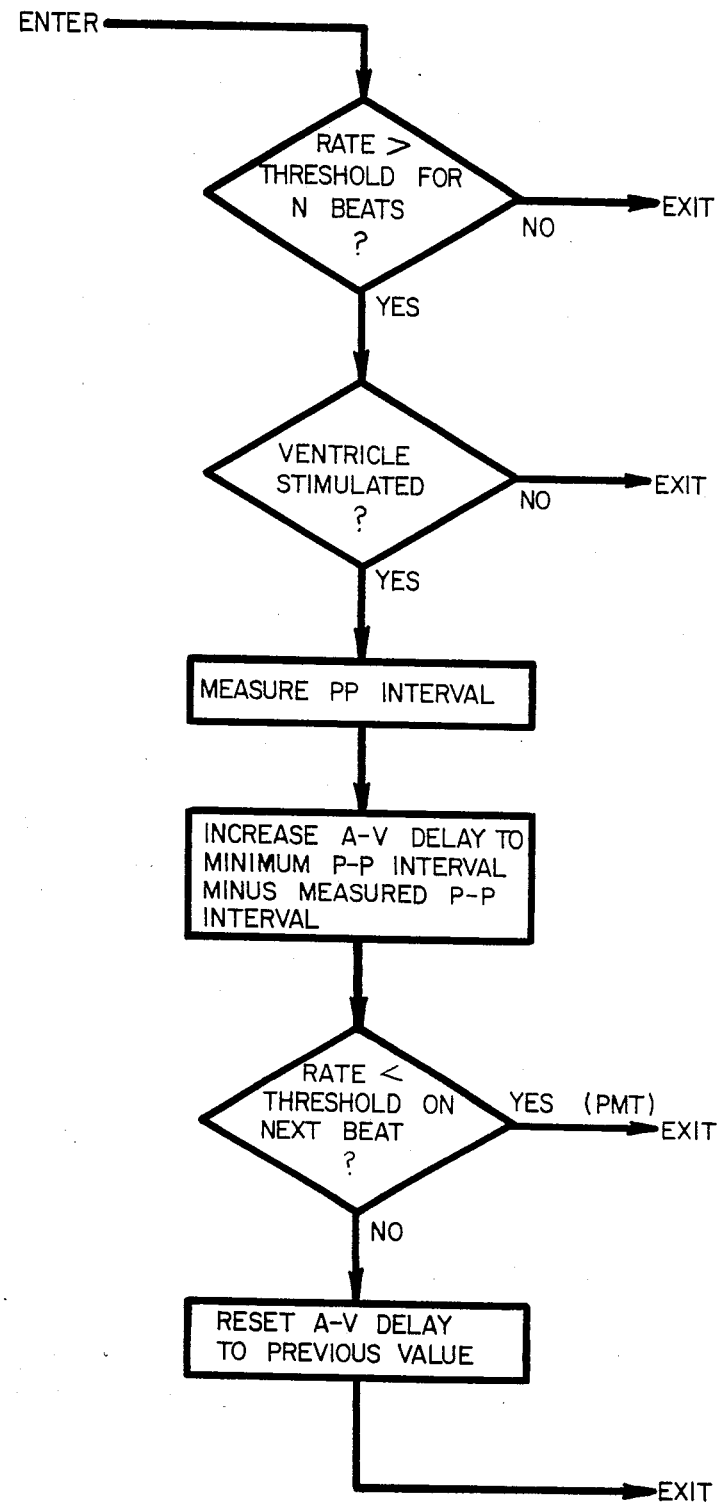
FIG. 7 is a flow diagram of another system for detecting pacer mediated tachycardia.

Referring to FIG. 7, another method of detecting pacer mediated tachycardia is illustrated. In the FIG. 7 embodiment, if the rate is detected to be greater than the threshold for four beats, then a determination is made whether the ventricle has been stimulated. If the ventricle has been stimulated, the sensed PP interval is measured. The AV delay is then increased to a desired minimum PP interval minus the actual measured PP interval. For example, assume the minimum desired PP interval is 1,000 milliseconds, the original AV delay is 200 milliseconds, and the actual measured PP interval is 500 milliseconds (the 200 millisecond AV delay plus a 300 millisecond retrograde false P wave). The 500 milliseconds is subtracted from the 1,000 milliseconds and the original AV delay is thus increased by 500 milliseconds resulting in a new AV delay of 700 milliseconds. A determination is then made whether the rate is less than the threshold on the next beat. If the rate is less than the threshold on the next beat, then there is pacer mediated tachycardia. However, the increase to the AV delay (which in this embodiment resulted in a 700 millisecond AV delay) effectively modified the operation of the pacer to prevent the rate from exceeding a selected maximum rate.

On the other hand, if the rate is greater than threshold on the next beat, the tachycardia was not pacer mediated and the AV delay is reset to its original value of, for example, 200 milliseconds.

Although illustrative embodiments of the invention have been shown and described, it is to be understood that various modifications and substitutions may be made without departing from the novel spirit and scope of the present invention.

What is claimed is:

1. A system for detecting pacer mediated tachycardia which comprises the steps of:
   sensing electrical input signals from the atrium;
   sensing electrical signals from the ventricle;
   providing a stimulating pulse to the ventricle, at a first predetermined time after an electrical signal from the atrium is sensed, if no electrical signal from the ventricle is sensed within said first predetermined time;
   selecting a threshold rate for the interval between sensed electrical signals from the atrium;
   detecting whether said threshold rate is exceeded for a selected number of electrical signals from the atrium;
   if said threshold rate is exceeded for said selected number of electrical signals from the atrium, then increasing said first predetermined time by a second predetermined time;
   then determining whether the interval between sensed electrical signals from the atrium has increased by said second predetermined time; and
   if the interval between sensed electrical signals from the atrium has increased by said second predetermined time, then indicating that pacer mediated tachycardia has occurred.

2. A system as described in claim 1, including the step of determining if a stimulating pulse has been provided to the ventricle prior to the step of increasing said first predetermined time by said second predetermined time.

3. A system as described in claim 2, wherein if the interval between sensed electrical signals from the atrium has increased by said second predetermined time, then providing an extended refractory period after sensing an electrical signal from the atrium to a time that is substantially beyond the ventricular stimulating pulse to mask the detection of a retrograde electrical signal in the atrium.

4. A system as described in claim 2, wherein if the interval between sensed electrical signals from the atrium has increased by said second predetermined time, then providing a stimulating pulse to the atrium within a selected short time after the detection of the retrograde electrical signal in the atrium to cause the depolarization of the reentry path and inhibit retrograde conducting following the next stimulating pulse to the ventricle.

5. A system for detecting pacer mediated tachycardia, which comprises the steps of:
   sensing electrical signals from the atrium;
   sensing electrical signals from the ventricle;
   providing a stimulating pulse to the ventricle, at a first predetermined time after an electrical signal from the atrium is sensed, if no electrical signal from the ventricle is sensed within said first predetermined time;
   selecting a threshold rate for the interval between sensed electrical signals from the atrium;
   detecting whether said threshold rate is exceeded for a selected number of electrical signals from the atrium;
   if said threshold rate is exceeded for the selected number of electrical signals from the atrium, then determining if a stimulating pulse has been provided to the ventricle;

if a stimulating pulse has been provided to the ventricle, then increasing said first predetermined time by a minimum desired time interval between sensed electrical signals from the atrium minus the actual sensed time interval between electrical signals from the atrium;

then detecting whether said rate is less than threshold for a subsequent heartbeat; and if said rate is less than threshold for a subsequent heartbeat, then pacer mediated tachycardia has occurred.

6. A system as described in claim 5, wherein if said rate is not less than threshold for a subsequent heartbeat, then reestablishing said first predetermined time interval.

7. A system as described in claim 5, wherein said first predetermined time comprises the AV delay and said minimum desired time interval between sensed electrical signals from the atrium comprises a minimum desired PP interval.

* * * * *